US007244583B2

(12) United States Patent
Sanders

(10) Patent No.: US 7,244,583 B2
(45) Date of Patent: Jul. 17, 2007

(54) DEVICE FOR DETECTING BACTERIAL CONTAMINATION AND METHOD OF USE

(75) Inventor: Mitchell C. Sanders, West Boylston, MA (US)

(73) Assignee: ECI Biotech Inc., Worcester, MA (US)

(*) Notice: Subject to any disclaimer, the term of this patent is extended or adjusted under 35 U.S.C. 154(b) by 141 days.

(21) Appl. No.: 11/036,761

(22) Filed: Jan. 14, 2005

(65) Prior Publication Data

US 2005/0181465 A1    Aug. 18, 2005

Related U.S. Application Data

(63) Continuation of application No. 09/848,781, filed on May 3, 2001, now abandoned.

(60) Provisional application No. 60/201,405, filed on May 3, 2000.

(51) Int. Cl.
*C12Q 1/04* (2006.01)
(52) U.S. Cl. .......................................... 435/34; 435/23
(58) Field of Classification Search ................. 435/34, 435/23
See application file for complete search history.

(56) References Cited

U.S. PATENT DOCUMENTS

| 4,897,444 | A | 1/1990 | Brynes et al. |
| 5,330,889 | A | 7/1994 | Monget |
| 5,512,445 | A | 4/1996 | Yang et al. |
| 5,518,894 | A | 5/1996 | Berg |
| 5,523,205 | A | 6/1996 | Cossart et al. |
| 5,662,905 | A | 9/1997 | Siadak et al. |
| 5,716,799 | A | 2/1998 | Rambach |
| 5,783,410 | A | 7/1998 | He et al. |
| 5,824,468 | A | 10/1998 | Scherer et al. |
| 5,932,415 | A | 8/1999 | Schubert et al. |
| 5,976,827 | A | 11/1999 | Jeffrey et al. |
| 5,994,059 | A | 11/1999 | Hogan et al. |
| 6,048,688 | A | 4/2000 | Korth et al. |
| 6,051,391 | A | 4/2000 | Schabert et al. |
| 6,235,285 | B1 | 5/2001 | Burnham |
| 6,284,517 | B1 | 9/2001 | Restaino |
| 6,294,177 | B1 | 9/2001 | Fattom |
| 6,342,581 | B1 | 1/2002 | Rosen et al. |

FOREIGN PATENT DOCUMENTS

| EP | 0 428 000 A1 | 5/1991 |
| EP | 0 430 608 A1 | 6/1991 |
| EP | 0 864 864 A1 | 9/1998 |
| EP | 0 122 028 A1 | 7/2002 |
| WO | WO 91/16336 | 10/1991 |
| WO | WO 97/28261 | 8/1997 |
| WO | WO 9728261 A1 * | 8/1997 |
| WO | WO 00/50872 A3 | 8/2000 |
| WO | WO 01/59149 A2 | 8/2001 |
| WO | WO 02/10433 A2 | 2/2002 |

OTHER PUBLICATIONS

Domann et al., Infect. Immun., 59:65-72, 1991.*
Altekruse S.F., et al., "Cheese-Associated Outbreaks of Human Illness in the United States, 1973 to 1992: Sanitary Manufacturing Practices Protect Consumers," *J. Food Prot.*, 61(10):1405-1407(1998).
Dalton C.B., et al., "An Outbreak of Gastroenteritis and Fever Due to *Listeria monocytogenesis* in Milk," *N. Engl. J. Med.*, 336(2): 100-105 (1997).
Domann E., et al., "Molecular Cloning, Sequencing, and Identification of a Metalloprotease Gene from *Listeria monocytogenes* That Is Species Specific and Physically Linked to Listeriolysin Gene," *Infection and Immunity*., 59(1):65-72 (1991).
Engel, L.S., et al., "*Pseudomonas aeruginosa* Protease IV Produces Corneal Damage and Contributes to Bacterial Virulence," *Invest. Ophthalmol. Vis. Sci.*, 39(3):662-665 ( 1998).
Ericsson, H., et al., "An Outbreak of Listeriosis Suspected To Have Been Caused By Rainbow Trout," *J. Clin. Microbiol.*, 35(11):2904-2907(1997).
From the Centers for Disease Control and Prevention. Update: Multistate Outbreak of Listeriosis—United States, 1998-1999. *JAMA*,281(4):317-318(1999).
Gottesman S., "Proteases and Their Targets in *Escherichia coli,*" *Annu. Rev. Genet.* 30: 465-506(1996).
Häse C.C. and Finkelstein, R., "Bacterial Extracellular Zinc-Containing Metalloproteases," *Microbiological Reviews.*,57(4):823-837(1993).
Liu Y., et al., "Use of a Fluorescence Plate Reader for Measuring Kinetic Parameters with Inner Filter Effect Correction," *Anal. Biochem.*, 267(2):331-335(1999).
Maeda H. "Role of Microbial Proteases in Pathogenesis," *Microbiol. Immunol.*, 40(10):685-699(1996).
Marquis H., et al. "Proteolytic Pathways of Activation and Degradation of a Bacterial Phospholipase C during Intracellular Infection by *Listeria monocytogenes,*" *J. Cell Biol.*, 137(6):1381-1392(1997).
Nair S. et al. "ClpE, a Novel Member of the HSP100 Family, is Involved in Cell Division and Virulence of *Listeria monocytogenes,*" *Mol. Microbiol.*, 31(1):185-196 (1999).
Pallen M.J. and Wren, B., "The HtrA family of serine proteases," *Mol. Microbiol.* 26(2) 209-221 (1997).

(Continued)

*Primary Examiner*—Robert A. Zeman
*Assistant Examiner*—Brian Gangle
(74) *Attorney, Agent, or Firm*—Hamilton, Brook, Smith & Reynolds, P.C.

(57) ABSTRACT

A device and method for detecting the presence or absence of a prokaryotic microorganism are provided, comprising the steps of identifying a protein, such as a microbial-specific protease that characterizes the presence of a specific prokaryotic microbe and thereby provides a marker for that microbe; detecting the protease that is a marker for the presence of a specific prokaryotic microbe by cleaving a substrate when the protease is present; and signaling the presence of that protease when cleavage has occurred. More specifically, the method comprises identifying at least one outer membrane protein or a secreted protein that is unique to a particular microbial pathogen such as for example *Listeria monocytogenes* and that is substrate specific.

6 Claims, 3 Drawing Sheets

OTHER PUBLICATIONS

Poyart C., et al., "The Zinc Metalloprotease of *Listeria monocytogenes* Is Required for Muturation of Phosphatidylcholine Phospholipase C: Direct Evidence Obtained by Gene Complementation." *Infect. & Immun.*, 61(4) 1576-1580 (1993).

Rodriguez M., et al., "*Evaluation of Proteolytic Activity of Microorganisms Isolated From Dry Cured Ham*," *J. Appl. Microbiol.*, 85(5): 905-912(1998).

Schwartz M.A., and Luna, E., "Binding and Assembly of Actin Filaments by Plasma Membranes from *Dictyostelium Discoideum.*" *J. Cell Biol.*, 102(6):2067-2075(1986).

Smith G.A., et al., "The Tandem Repeat Domain in the *Listeria monocytogenes* ActA Protein Controls the Rate of Actin-based Motility, the Percentage of Moving Bacteria, and the Localization of Vasodilator-Stimulated Phosphoprotein and Profilin." *J. Cell Biol.*, 135(3): 647-660 (1996).

Trivett T.L.and Meyer, E., "Citrate Cycle and Related Metabolism of *Listeria monocytogenes*," *J. Bacteriol.* 107(3):770-779 (1971).

Vollmer P., et al. "Novel Pathogenic Mechanism of Microbial Metalloproteinases: Liberation of Membrane-Anchored Molecules in Biologically Active Form Exemplified by Studies with the Human Interleukin-receptor." *Infection and Immunity.*,64(9):3646-3651(1996).

Wang, Y-L, et al., "Analysis of Cytoskeletal Structures by Microinjection of Fluroescent Probes," *Eds. S. Grinstein and K. Foskett, in Noninvasive Techniques in Cell Biology*, pp. 177-212 (1990).

Thompson, J.S., et al., "Rapid Biochemical Test To Identify Verocytotoxin-Positive Strains of *Escherichia coli* Serotype O157," *J. Clin. Microbiol.* 28(10): 2165-2168 (1990).

Keelan, S.L. and Flower, R., v"Multitest System for Biochemical Identification of *Salmonella, Escherichia coli*, and Other *Enterobacteriaceae* Isolated from Foods: Collaborative Study," *J. Assoc. Off. Anal. Chem.* 71(5): 968-972 (1988).

Braun, V. and Schmitz, G., "Excretion of a Protease by Serratia Marcescens," *Arch. Microbiol.*, 124:55-61, (1980).

Decedue, C.J., et al., "Purification and Characterization of the Extracellular Proteinase of Serratia Marcescens," *Biochim. Biophys. Acta*, 569:293-301, (1979).

Kennedy, E.P. and Scarborough, G.A., "Mechanism of Hydrolysis of O-Nitrophenyl-β-Galactoside in *Staphylococcus aureus* and Its Significance for Theories of Sugar Transport," *Proc. Natl. Acad. Sci. USA*, 58:225-228 (1967).

Molla, A., et al., "Characterization of 73kDa Thiol Protease from Serratia Marcescens and Its Effect on Plasma Proteins," *J. Biochem.*, 104:616-621, (1988).

Molla, A., et al., "Degradation of Protease Inhibitors, Immunoglobulins, and Other Serum Proteins by Serratia Protease and Its Toxicity to Fibroblasts in Culture," *Infection and Immununity*, 53:522-529, (1986).

Oshida, T., et al., "A *Staphylococcus aureus* Autolysin That Has an N-Acetylmuramoyl-L-Alanine Amidase Domain and an Enod-β-N-Acetylglucosaminidase Domain: Cloning, Sequence, Analysis, and Characterization," *Proc. Natl. Acad. Sci. USA*, 92:285-289, (1995).

Rice, K., et al., "Desciption of *Staphylococcus* Serine Protease (*ssp*) Operon in *Staphylococcus aureus* and Nonpolar Inactivation of *sspA*-Encoded Serine Protease," *Infection and Immunity*, 69:159-169, (2001).

Rosenstein, R. and Götz, F., "*Staphylococcal* Lipases: Biochemical and Molecular Characterization," *Biochimie* 82:1005-1014, (2000).

Salamone, P.R. and Wodzinski, R.J., "Production, Purification and Characterization of a 50-kDa Extracellular Metalloprotease From Serratia Marcescens," *Appl. Microbiol. Biotechnol.*, 48:317-324, (1997).

Shikata, S., et al., "Detection of Large COOH-Terminal Domains Processed From the Precursor of Serratia Marcescens Serine Protease in the Outer Membrane of *Escherichia Coli*," *J. Biochem.*, 111:627-632, (1992).

Sugai, M., et al., "Identification of Endo-β-N-Acetylglucosaminidase and N-Acetylmuramyl-L-Alanine Amidase as Cluster-Dispersing Enzymes in *Staphylococcus aureus*," *J. Bacteriol.*, 177:1491-1496, (1995).

van Kampen, M.D., et al., "Modifying the Substrate Specificity of Staphylococcal Lipases," *Biochem.*, 38:9524-9532, (1999).

Zahner, D. and Hakenbeck, R., "*The Streptococcus pneumoniae* Beta-Galactoside Is a Surface Protein," *J. Bacteriol.*, 182:5919-5921, (2000).

Zhong, W. and Benkovic, S.J. "Development of an Internally Quenched Fluorescent Substrate for *Escherichia coli* Leader Peptidase," *Analytical Biochemistry*, 255:66-73 (1998).

O'Riordan, M., et al., "Listeria Intracellular Growth and Virulence Require Host-Derived Lipoic Acid," *Science*, 302:462-464 (2003).

Glaser, P., et al., "Comparative Genomics of Listeria Species," *Science*, 294:849-852 (2001).

Okuno, K., et al., "An Analysis of Target Perferences of *Excherichia coli* Outer-Membrane Endoportease OmpT for Use in Therapeutic Peptide Production: Efficient Cleavage of Substrates with Basic Amino Acids at the P4 and P9 Positions," *Biotechnol. Appl. Biochem.*, 36:77-84 (2002).

Yolken, R. H., "Enzymic Analysis for Rapid Detection of Microbial Infection in Human Body Fluids: An Overview," *Clin. Chem.* 27(9): 1490-1498 (1981).

\* cited by examiner

```
                              SEQUENCE LISTING

<160> NUMBER OF SEQ ID NOS: 5

<210> SEQ ID NO 1
<211> LENGTH: 9
<212> TYPE: PRT
<213> ORGANISM: Listeria monocytogenes

<400> SEQUENCE: 1

Asn Met Leu Ser Glu Val Glu Arg Glu
 1               5

<210> SEQ ID NO 2
<211> LENGTH: 11
<212> TYPE: PRT
<213> ORGANISM: Listeria monocytogenes

<400> SEQUENCE: 2

Ala Cys Cys Asp Glu Tyr Leu Gln Thr Lys Glu
 1               5                  10

<210> SEQ ID NO 3
<211> LENGTH: 11
<212> TYPE: PRT
<213> ORGANISM: Listeria monocytogenes

<400> SEQUENCE: 3

Ala Asp Thr Val Glu Pro Thr Gly Ala Lys Glu
 1               5                  10

<210> SEQ ID NO 4
<211> LENGTH: 30
<212> TYPE: DNA
<213> ORGANISM: Listeria monocytogenes

<400> SEQUENCE: 4
```

-continued

```
catgccatgg gtagaacggg ctgataccca                              30

<210> SEQ ID NO 5
<211> LENGTH: 32
<212> TYPE: DNA
<213> ORGANISM: Listeria monocytogenes

<400> SEQUENCE: 5
gcgccggaat tctcagttaa ccccaactgc tt                           32
```

DEVICE FOR DETECTING BACTERIAL CONTAMINATION AND METHOD OF USE

RELATED APPLICATIONS

This application is a continuation of U.S. application Ser. No. 09/848,781, filed May 3, 2001 (now abandoned), which claims the benefit of U.S. Provisional Application No. 60/201,405, filed on May 3, 2000 (now abandoned). The entire teachings of the above applications are incorporated herein by reference.

FIELD OF THE INVENTION

The present invention relates to the detection of prokaryotic microorganisms. In particular, the present invention relates to a method and a device for detecting the presence or absence of a prokaryotic microorganism or pathogen that contaminants food and food related work areas.

BACKGROUND OF THE INVENTION

Presently, the United States Department of Food Safety and Inspection Services (FSIS) spend over half a billion dollars annually on meat, poultry, and fish inspections for bacterial contaminants. Broadly, the inspections are used to determine the cleanliness of the work area and to detect pathogenic microbes in foodstuffs. Ingestion of pathogenic microbes can result in food poisoning when the microbes are inadvertently packaged into supermarket goods. One example of a pathogenic microbe is *Salmonella*. *Salmonella* is a genus of gram-negative bacterium that is a major source of human foodborne illness worldwide. Up to 4 million cases of salmonellosis are reported each year in the United States alone. A number of different serotypes of pathogenic *Salmonella* are known, the most common of which are *S. typhimurium* and *S. enteriditis*. Typically, salmonellosis is treated with antibiotics. However, antibiotic resistant strains of *Salmonella* are emerging. *Listeria* and *E. coli* are also commonly occurring microbial contaminants. *Listeria monocytogenes* is a gram-positive bacterium that is a common cause of gastroenteritis. Tests for *E. coli* are performed as an indication of fecal contamination of food and work areas.

The food industry has tended to test for food contamination at the production and wholesale level only. However, between the time a foodstuff is packaged and consumption occurs, a bacterial pathogen that was undetectable at the wholesale check can multiply and can thus become a health hazard. Contaminated food is increasing in importance for the producer. Bad publicity and product recalls cost the food industry millions of dollars each year.

Currently, the assay systems used at the wholesale and production level require specialized training and equipment, are time consuming, and are not very sensitive to the presence of small numbers of pathogenic bacteria. To assay for suspected bacterial contamination, a culture is obtained using a sample of the food or from the workplace that is suspected of being contaminated in order to increase the amount of detectable substance (suspected bacterial contaminant). Culturing may require up to 48 hours. Then, the cells grown in the culture are lysed to produce a lysate. Historically, assaying for pathogenic bacteria has been done using antibodies in an immunoassay for detecting bacterial proteins in the lysate. In recent years, some companies have used a polymerase chain reaction (PCR) based methods to replicate microbial genetic material for use in detection assays. The isolated genetic material is multiplied and identified in separate steps. The PCR detection system also requires hours rather than minutes to perform. Testing is performed at the time of or before shipping a product to the supermarket. A simple, sensitive, and rapid method for detecting food contamination is required both for testing at the wholesale level and at the retail level.

Detection devices are also needed at the retail level to protect the consumer. Testing apparatus useful at the wholesale level generally is not useful at the retail level for various reasons. First, most wholesale level tests require technical skills not often practiced by the typical consumer. Second, when a product remains on the shelf before purchase, contaminant levels can increase, especially if the temperature of the product is not appropriately controlled. During the time the food is in transit, bacterial growth can occur. Methods and devices for detecting microorganisms in food at the retail level have been set forth. While tests have been developed for the retail market, they have failed to be adopted. Colorimetric detectors of changes in ionic content, for example pH, of the liquid or material surrounding the food product have been used on or incorporated into retail packaging such as illustrated in U.S. Pat. Nos. 4,746,616 and 5,053,339, the disclosures of each of which are incorporated herein by reference. Antibodies have also been coupled to calorimetric labels for detection of contaminates such as illustrated in U.S. Pat. Nos. 5,306,466 and 5,869,341, the disclosures of each of which are incorporate herein by reference. None of the aforementioned are sufficiently specific and sensitive to meet the needs of the current marketplace.

A means for specifically and sensitively detecting the presence or absence of at least one pathogenic microorganism in potentially contaminated food products at the retail level is needed.

SUMMARY OF THE INVENTION

The present invention provides a method for detecting the presence or absence of a prokaryotic microorganism comprising the steps of identifying a bacterial-specific protein, such as a protease that characterizes the presence of a specific prokaryotic microbe and thereby provides a marker for that microbe; detecting the protease that is a marker for the presence of a specific prokaryotic microbe by cleaving a substrate when the protease is present; and signaling the presence of that protease when cleavage has occurred. More specifically, the method comprises identifying at least one outer membrane protein or a secreted protein that is unique to a particular microbial pathogen such as for example *Listeria monocytogenes* and that is substrate specific.

Utilizing a bioinfomatic approach, BLAST search comparisons of the protease complements of a plurality of common pathogenic bacterial species were made. One or more proteases that were unique to a species were identified. Next the specific substrate for each protease was identified using fluorescence resonance energy transfer (FRET). The unique, identified substrate was then labeled and used to detect the presence of a particular microbial pathogen in samples requiring testing. Identified protease substrates were tested with common foods and yeast in order to identify substrates that are specific to the bacteria.

In another aspect, the present invention provides a device for detecting the marker protein and for notifying a consumer of the presence of the marker protein. A biosensor for use in retail stores or home-use to detect contaminated food comprising a specific substrate that is coupled to packaging material proximal to the food stuff to be monitored for bacterial contamination is provided. Preferably, the substrate is covalently bound to a label and thus has a detection signal that upon proteolysis of the substrate-label bond indicates the presence of the contaminating bacteria. The biosensor is made by first determining the specific substrate of a specific protease characteristic of the bacteria to be detected. The determined specific substrate is labeled with a plurality of chromatogenic or fluorescent leaving groups. Most preferably, the labeling group provides a latent signal that is activated only when the signal is proteolytically detached from the packaging. Chromatogenic leaving groups are, for example, para-nitroanalide groups. Preferably, labeled substrate molecules are coupled to the interior surface of the packaging material proximal to the foodstuff. Should the foodstuff become contaminated, the microbial pathogen produces protease which acts on the labeled substrate that is attached to the packaging, liberating the leaving group. When a visually detectable calorimetric signal is released, this results in a visible color change at the site of interest.

In another embodiment, proteases that are common among pathogenic microbial species, but that are substrate specific and that share a common substrate, are identified for use in a method and a device to detect the presence of bacteria. For example, bacteria can collect on work surfaces in meat plants and in restaurants. A substrate that can be cleaved by a plurality of bacteria is labeled and covalently bound to a collector substrate, such as cotton fibers on the tip of a swab. The swab tip is used to wipe the surface suspected in being contaminated by bacteria. The swab tip is placed in a medium and incubated using conditions that allow proteolysis of the labeled substrate if the protease(s) specific for the bound, labeled substrate is present. Proteolysis results in the production of a detectable signal, for example a color change, may be visible if the signal is a chromatogenic leaving group.

In yet another embodiment of the present invention, a strip sensor is provided. Preferably, the strip sensor comprises an inert material to which a substrate having a latent detection signal has been covalently attached. A single protease substrate or a plurality of protease substrates may be utilized. When a plurality of protease substrates are utilized, each may be labeled so as to distinguish it from another and/or each may be localized in a particular region on the strip support material. Depending upon the foodstuff, one can predict the frequency of expected occurrence of a particular pathogenic microbe. For example, *Listeria monocytogenes* is a common contaminant of poultry products, therefore, a chromagenic leaving group labeled substrate specific for a *Listeria monocytogenes* protease may be incorporated onto the surface of the packaging proximal to the poultry product. However, where multiple possible microbial pathogens may be present, a substrate that may be proteolyzed by all of the microbes may be utilized as long as it is specific to the pathogenic microbes.

In still another aspect of the present invention, a kit is provided for detecting microbial food contaminants. The kit comprises a flat solid support, preferably having a plurality of wells, to which a protein substrate labeled with leaving groups is linked. A means for providing a phosphate buffered solution, a negative control, and a positive control are provided. A sample of suspect food (SF) is prepared in phosphate buffer. An aliquot of each of SF, negative control, and positive control is placed in its own well and allowed to react. Those wells where a color change is observed contain microbial contaminant unless the negative control well also changes color. If the negative control well changes color, then the assay may be repeated.

DETAILED DESCRIPTION OF THE INVENTION

One of the most important considerations for developing a wholesale test kit is the ability to capture microbial pathogens in foods. It is necessary to have a procedure for reliably capturing bacteria from food matrices in such a way that all of the viable bacteria are captured and enriched in a suitable recovery medium. Many companies use cotton swabs or filters to capture the bacteria, but several independent studies have shown that entrapment of bacteria in these porous materials reduces the accuracy of detecting low level contamination. Standard filter capture methods also entrap bacteria but are less reliable. than straight-forward plating, and culture methods take up to a week to obtain results. Bacterial capture devices such as magnetic beads are more costly and require an additional step to collect the bacteria along the wall of the tube with a magnet.

In food safety testing, the food sample is ground up in a special blender called a stomacher blender, which is fitted with a sterile stomacher bag. The basic principle of the inventive capture method is to add a PES tablet to the blended sample for a few minutes with gentle shaking to capture the bacteria. The shell remains intact during this short exposure time at room temperature. After the bacteria are captured, the PES is allowed to float to the top of the stomacher bag from which it is removed with sterile forceps. The tablet is placed in growth enrichment medium and incubated at 37° C. until sufficient bacteria can be reliably detected. After sufficient time at 37° C., the gelatin coat dissolves and the bacteria are effectively released into the growth culture medium.

Figure 1:
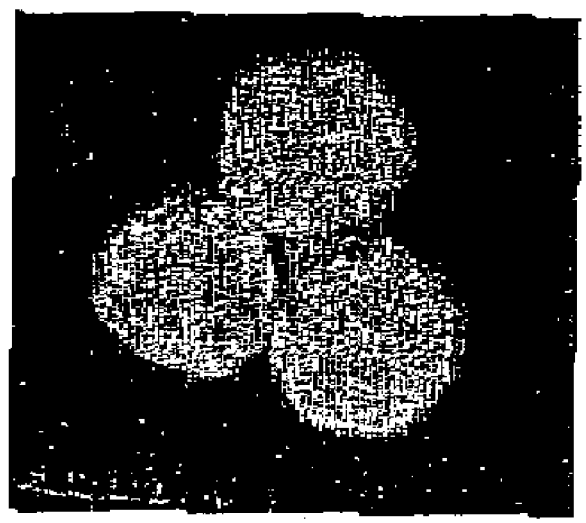
FIG. 1 is an image of the Protein Encapsulated Styrofoam (PES) for capturing bacteria such as *L. monocytogenes;*
Figure 2:
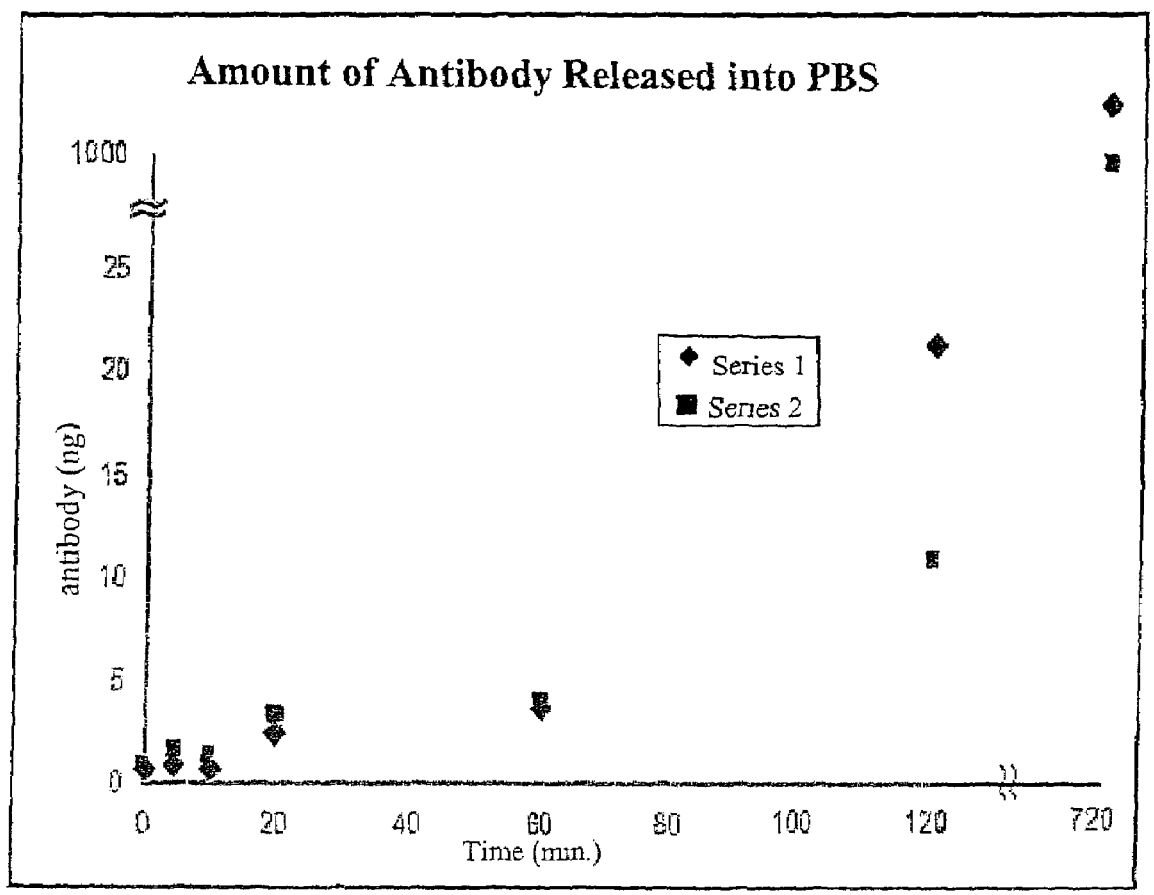
FIG. 2 is a graph showing the dissolving time of PES tablets as determined by the amount of antibody released with time.

To form the PES tablet, gelatin was heated to 65° C. and allowed to cool to about 55° C. Then 50 μg/ml of antibody was added just before the gelatin capsule formed around the pellet. The PES technology can be used to capture and release bacteria from a test sample into enrichment medium. The rigidness of the gelatin prevents the antibodies from being released until several hours after incubation (see FIG. 2).

Two PES tablets were incubated in PBS with vigorous shaking at room temperature (RT; series 1 and 2). At each time point (0, 5, 10, 20, 60, 120, and 720 minutes), an aliquot of the sample was removed and the amount of HRP conjugated antibody was detected with TMB-peroxidase substrate (KPL, Gaithersburg, Md.). The samples were read with a Benchmark microplate reader at 655 rm. After 20 minutes, less than 1% of the total antibody on the PES tablet has dissolved into the PBS solution. Thus it is possible to capture bacteria with the antibody-coated capsules and release them into the enrichment media with this method. The rigidness (high bloom number) of the pig skin gelatin (300 bloom) makes this capture and release procedure possible. Using a lower bloom gelatin would allow for the bacteria to be released faster into the enrichment media.

The present invention provides a method to quantitatively capture and release contaminating bacteria present in a food sample that utilizes the protein-encapsulated Styrofoam (PES) tablets described above. One or more tablets coated with commercially available antibodies entrapped in gelatin can be placed in a homogenized food test sample in a stomacher bag and incubated with gentle shaking at room temperature. The tablet can then be removed with sterile forceps and placed in growth medium at 37° C. for a short period of time, until the gelatin coat dissolved and released the bacteria into the medium.

The presence of *L. monocytogenes* contamination is detected by measuring the metalloprotease (mpl), which is found only in the pathogenic species of *L. monocytogenes* (Domann et al., infection and Immunity. 1991. January; 59(1):65-72; Mengaud et al., 1991). A series of peptides, M1 (lot 038-13/15) and P1 (lot 038-10/12), for use as synthetic substrates for mpl (Table 1) was designed and the sequences manufactured by New England Peptide (195 Kimball St., Fitchburg, Mass.). The peptides were synthesized with fluorescent groups (DABCYL and EDANS) in such a way that the active sites were not blocked. The M1 peptide is specific for *L. monocytogenes* at pH 5.5.

TABLE 1

First set of peptides used as probes for FRET analysis of mpl activity

| Peptide | Amino acid sequence | MW | Description |
|---|---|---|---|
| M1 | DABSYL-NML, SEVERE-EDANS | 1642 | Specific to Listeria at pH 5.5 |
| P1 | DABSYL-ACCDEYLQTKE-EDANS | 1838 | Substrate with broad pathogen specificity |
| P2 | DABSYL-ADTVEPTGAKE-EDANS | 1653 | Not cleaved by Listeria or *E. coli* |

(peptide M1 = SEQ ID NO. 1; P1 = SEQ ID NO. 2; P2 = SEQ ID NO. 3)

Figure 3A:
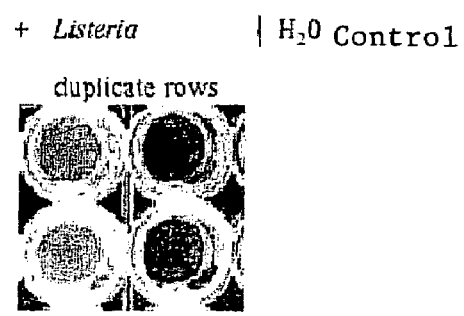
FIGS. 3A and 3B are images that demonstrates the fluorescence activation of a substrate in the presence of *L. monocytogenes.*
Figure 3B:
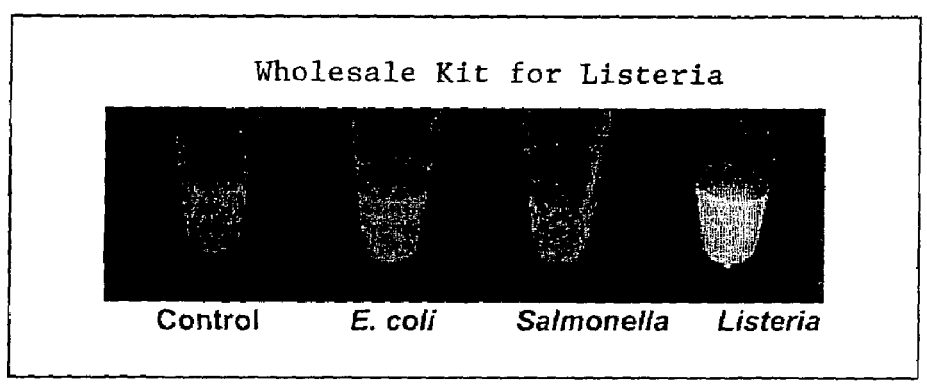

Preliminary evidence indicates that at pH 5.5, the M1 peptide is specific for *L. monocytogenes* and does not significantly detect the presence of *E. coli* (see FIG. 3). It is expected that this peptide and derivatives of this peptide (with one or two amino acid substitutions) could be used for a standard microplate assay format for *L. monocytogenes* in foods.

It was discovered that *Listeria monocytogenes* secretes at least two characteristic proteases, one of which is a metalloprotease and one that is a serine protease. Microbial proteases can be separated into four major classes based on the catalytic site (metallo, serine, cysteine, and aspartate proteases). The particular type of catalytic site may be determined using catalytic site blockers. For example the presence of a metalloprotease having a metallo catalytic site can be demonstrated by specifically blocking the catalyzed reaction with TAPI [N-{D,L-[2-(hydroxaminocarbonyl)methyl]4-methylpentanoyl}L-3-(2inapthyl)alanyl-L-alanine, 2-aminoethyl amide]. The catalytic site of each protease has a characteristic amino acid signature, motif, or amino acid sequence that can be used to identify that protease and similar new proteases within a class thereof. In addition, many of the proteases have two forms: a larger inactive form that requires partial proteolysis (limited proteolysis) to obtain a smaller active form of the enzyme. Proteases are known to break the peptide bonds in a protein substrate. Some proteases are known to be very specific with regard to the type of peptide bond that they are able to hydrolyze or break. When a protease is limited with respect to the bond(s) it can break, the protease is said to be substrate specific.

The amino acid sequence characteristic of a particular enzyme or of its catalytic site is reproduced from the genetic code. Knowing the amino acid sequence of an enzyme or of its catalytic site, one can deduce the nucleotide sequence in the DNA or RNA that codes for that sequence. The nucleotide sequence can then be located in the genetic code of a bacterium or it can be synthesized. Cloning of the genetic sequence coding for the amino acid sequence can be used to provide multiple templates for generating copies of the enzyme or its catalytic site. Using these copies of the enzyme or its catalytic site, the exact site of cleavage or type of bond hydrolyzed can be determined. Using this information, a specific substrate of the enzyme can be defined. This substrate can be used to assay for the presence of the pathogenic bacteria. The substrate is provided with a label that serves to signal the presence of the pathogenic bacteria. The preferred label is chromagenic and produces a visual, signal when cleaved. For example, when determining specific cleavage of a substrate, the substrate can be provided with two different dyes, where one serves to quench the other when the dyes are in close proximity and measured by FRET.

Fluorescence resonance energy transfer (FRET) is the process of a distance dependent excited state interaction in which the emission of one fluorescent molecule is coupled to the excitation of another. A typical acceptor and donor pair for resonance energy transfer consists of 4-[[4-(dimethylamino)phenyl]azo]benzoic acid (DABCYL) and 5-[(2-aminoethylamino]naphthalene sulfonic acid (EDANS). EDANS is excited by illumination with 336 nm light, and emits a photon with wavelength 490 nxn. If a DABCYL moiety is located within 20 angstroms of the EDANS, this photon will be efficiently absorbed. DABCYL and MANS will be attached to opposite ends of a peptide substrate. If the peptide is intact, FRET will be very efficient. If the peptide has been cleaved by the metalloprotease, the two dyes will no longer be in close proximity and FRET will be inefficient. The cleavage reaction can be followed by observing either a decrease in DABCYL fluorescence or an increase in EDANS fluorescence (loss of quenching).

Alternative methods for providing a visual signal include labeling the protease substrate with a food safe dye (FD&C) such as Texas red or with amido black or with a fluorometric dye such as 4-nitroanaline or 7-amino-4-methyl coumarin. For retail applications, labeled substrate may be bound to the food packaging. When the protease characterizing the pathogenic microorganism is present, the label or the labeled substrate is cleaved from the packaging, diffusing from its attached site. This results in a color change at that site. For example, the packaging may have "DO NOT EAT" printed in red thereon. When the labeled substrate is present, the writing is masked. When the label is removed, the warning becomes visible.

In one embodiment, an assay system that detects and signals the presence of pre-determined prokaryotic microorganisms is provided. Detection of *Listeria monocytogenes* is exemplified. However, the invention is not intended to be limited to that pathogenic species. The presence of the pre-determined prokaryotic organism of interest is indicated by proteolytic cleavage of a substrate by a protease that results in the production of a signal. Preferably, the signal is chromogenic. *L. monocytogenes* (DP-L1955) was kindly provided by Dr. Julie Theriot of the Stanford School of Medicine. The *L. monocytogenes* was made avirulent by a deletion of the gene required for intracellular motility (ActA, Smith et al., J. Cell Biol. 1996 November; 135(3):647-60).

A method for developing an assay for detecting a pathogenic bacteria that produces at least one extracellular protease and a method for using the assay to detect pathogenic bacteria producing at least one extracellular protease follows:

Step 1) Define a catalytic marker amino acid sequence that uniquely identifies the prokaryotic microorganism of interest.

Select an amino acid sequence, also termed a marker sequence, that uniquely characterizes or marks the presence of the microorganism of interest, such as, for example, an amino acid sequence unique to an extracellular protease produced by a pathogenic prokaryotic microorganism of interest. The selection is performed utilizing a bioinfomatic approach. BLAST search comparisons among common pathogenic bacterial species with respect to known amino acid sequences are made. One or more amino acid sequences that are unique to a specific prokaryotic microorganism are determined.

Step 2) Obtain sufficient protease to determine conditions facilitating optimal proteolysis by the protease.

Isolate the protease from the extracellular medium in which the pathogenic bacteria to be assayed is growing.

Alternatively, if the genetic sequence for the protease or the location of the genetic sequence for the protease are unknown, isolate and clone the genetic sequence that results in the expression of the marker amino acid sequence of Step I, or, first determine the genetic sequence, and then proceed as before.

Step 3) Determine the conditions for growth of the prokaryotic organism and for the production of extracellular protease.

Determine medium required for growth of the specific prokaryotic microorganism of interest and for expression of its unique active protease into the medium.

Determine whether a second protease is required to convert the specific protease from an inactive precursor form to an active form.

To determine if the protease has been secreted in an active form, a sample of the bacterial culture is provided with chosen potential substrates and cleavage of these substrates is determined. For example, a bacterial pellet from Step 3 is gently resuspended in 500 μl of DMEM in the presence of common extended substrates (myosin II, bovine serum albumin, collagen, fibronectin, and hemoglobin). Myosin II, but not the proteins from milk such as casein, has been shown to be a suitable substrate to measure the proteolytic activity of gram positive bacteria isolated from dried cured ham (Rodrigez et al., Appl. Microbiol. 1998. Novemeber; 85(5):905-12). The suspension of bacteria and substrates is incubated at 37° C. with gentle shaking. At preset times (0.1, 0.3, 1.0, 3.0, 5.0, 24, and 48 hours) the samples are centrifuged to spin down the bacteria, and a small aliquot is removed for a SDS-PAGE gel sample. After completion of the time course the samples are run on a 10-15% gradient SDS-PAGE minigel. Then, the proteins are transferred to IMMOBILON® Pseq (Transfer buffer, 10% CAPS, 10% methanol pH 11.0, 15 V for 30 minutes) using a BIO-RAD semi-dry transblotting apparatus. Following transfer of the proteins, the blot is stained with Coomassie blue R-250 (0.25% Coomassie Brilliant Blue R-250, 50% methanol, 10% acetic acid) and destained (high destain for 5 minutes, 50% methanol, 10% acetic acid; low destain until complete, 10% methanol, 10% acetic acid) followed by sequencing from the N-terminal. Alternatively, the samples will be run on a mass spectrometer in order to map the sites of proteolytic cleavage using a Voyager Elite Mass spectrometer (Perspective Biosystems).

For example, an extracellular metalloprotease is produced by *L. monocytogenes*, designated mpl. The gene for this protease is just downstream of another virulence factor, the listerolysin gene (Domann et al., Infection and Immunity. 1991. January; 59(1):6572). Mpl has two forms, active and inactive. The three possible mechanisms for activation of mpl or any inactive protease by limited proteolysis are: auto-digestion (autocatalytic processing), digestion by a bacterial protease other than the metalloprotease, and digestion by an extracellular host cell protease. Metalloprotease activity has been found to be indirectly measurable in the supernatants of *L. monocytogenes*. Mpl activity can be monitored by measuring the shedding of IL-6 receptor from the surface of human monocytes. Processing of the precursor metalloprotease of *L. monocytogenes* to the mature form was determined to require the presence of the monocytes.

The following method can be used to test activation of an inactive protease of other pathogenic bacteria. Preincubate the bacteria of interest with either methanol fixed whole cells or NaOH stripped membrane preparations of monocytes. Fixation of the monocytes will prevent the bacteria from internalizing. Briefly, 10,000 CFU of *L. monocytogenes* is added to nearly confluent dishes of monocytes that are fixed with minus 20° C. 100% methanol for 10 minutes or 5.0% paraformaldehyde in a buffer that preserves the cytoskeleton. After 2-4 hours of incubation, the supernatant containing bacterium is removed and is centrifuged to separate the supernatant from the cell pellet. The supernatant is incubated with chosen protein substrates for preset times to determine its activity.

*L. monocytogenes* expression of active metalloprotease was found to be enhanced by growing the prokaryotic bacteria in a protein free medium such as D10 medium, a medium developed by Trivett and Meyer (1971). The bacteria were cultured overnight (24 hrs); centrifuged at 5K×g for 10 minutes and then resuspended in the tissue culture medium (Dulbecco's Modified Eagle Medium, "DMEM", Life Technologies (Gaithersburg, Md.).

Step 4) Identify any specific protein and/or peptide substrate(s) of the active species-specific protease.

Step 5) Increase the specificity of the protease-substrate interaction (optional) by determining the active or binding site of the protease, then determining the genetic sequence useful for producing that active or binding site, and cloning the determined genetic sequence.

Identify the target site(s) also termed the "active site(s)" for cleavage by the protease.

Determine the peptide sequence for the active site of the protease using fluorescence resonance energy transfer (FRET). Fluorescence resonance energy transfer (FRET) is the process of a distance dependent excited state interaction in which the emission of one fluorescent molecule is coupled to the excitation of another. FRET is one of the best ways to identify the substrate specificity for a particular protease (Liu et al., Anal Biochem. 1999. February 15; 267(2):331-5). A typical acceptor and donor pair for resonance energy transfer consists of 4-[[4'-(dimethylamino) phenyl]azo]benzoic acid (DABCYL) and 5-[(2iaminoethylamino]-naphthalene sulfonic acid (EDANS). MANS is excited by illumination with 336 nm light, and emits a photon with wavelength 490 nm. If a DABCYL moiety is located within 20 angstroms of the EDANS, this photon will be efficiently absorbed. DABCYL and EDANS will be attached to opposite ends of a peptide substrate. If the peptide is intact, FRET will be very efficient. If the peptide has been cleaved by the metalloprotease, the two dyes will no longer be in close proximity and FRET will be inefficient. The cleavage reaction can be followed by observing either a decrease in DABCYL fluorescence or an increase in EDANS fluorescence (loss of quenching).

When the enzyme is a metalloprotease (mpl), the active form of the mpl can be amplified by polymerase chain reaction using forward and reverse primers containing useful restriction sites for cloning into an expression vector with a strong inducible promoter (such as the T7 system of pET-28a, NOVAGEN). Userful primers for the amplification are catgccatgggtagaacgggctgataccca (SEQ ID NO. 4) and gcgccggaattctcagttaaccccaactgctt (SEQ ID NO. 5). Each primer has at least a 6 base pair overhang. The DNA is amplified from either lysed colonies of *L. monocytogenes* or from purified preparations of genomic DNA from *L. monocytogenes*. The forward primer is provided with a Nco I site that includes the start methionine (CATATG). The reverse primer includes a stop codon (TGA) and an Eco RI restriction site (GAATTC). A typical amplification protocol comprises amplifying the genetic sequence with Taq polymerase under the following conditions: 92° C. initial melt 4 minutes (25 cycles, 50° C. anneal 30 seconds, 72° C. extension 1.5 minutes, 92° C. melt 30 seconds), 72° C. final extension 10 minutes and 4° C. store. The annealing temperature may be increased or decreased somewhat to account for the predicted melting temperature (Tm) of the primers. Following cloning of the genetic sequence for the active metalloprotease into pET28a, the gene is sequenced by double stranded primer walk sequencing on an ABI310 genetic analyzer. The recombinant active form of the metalloprotease genetic sequence is purified by nickel-nitrilotriacetic acid chromatography by taking advantage of the polyhistidine tag in the pET-28a vector.

Step 6) Provide a device with a peptide substrate having a labeled carboxy terminus where cleavage thereof has been determined to be specific by the FRET assay of Step 5 to the protease of the pathogenic bacteria of interest.

For example, a chromagenically labeled peptide could be bound to a polyvinylidene fluoride (PVDF) membrane with a hydrophobic area. When the peptide is clipped, the dye would concentrate in the hydrophobic area, becoming visible. Alternatively, the peptide could be labeled fluorescently, and visualized with a UV lamp. Another possibility is a peptide with a chromagenic leaving group that upon removal changes color. The peptide may be labeled with a blue dye, coupled to a red surface. To the observer, the surface would look black unless the specific bacteria were present to provide protease that would cleave the peptide, turning the surface red as the peptide was proteolysed and diffused away. Although conventional leaving groups such as 4-nitroanaline or 7-amino-4-methyl-coumarin can be quantified spectrophotometrically and fluorometrically, it may be best to use a leaving group such as Texas Red that has an intense blue color. By placing two or three Texas Red groups near the end of the peptide, it would be possible to detect visually the clearance of the substrate by *L. monocytogenes* protease activity.

The cysteines at carboxyl terminus of the peptides were labeled with Texas Red bromoacetamide using a standard procedure described for labeling actin. See Wang and Sanders, 1990. An example is a hydrophobic peptide labeled with 2-3 Texas Red molecules. Another possibility would be to label the peptide with Amido black. As the substrate is proteolysed by mpl, the black peptide diffuses away, and a clear zone would appear indicating the presence of *L. monocytogenes*.

The peptide can be coupled to a surface such as a glass microtiter plate or a polypropylene food packaging material in the proper orientation. The microtiter plate should provide a plurality of derivatized binding sites for coupling to the peptide substrate such as succimidyl ester labeled primary amine sites on derivatized plates (Xenobind plates, XENOPORE®).

By maintaining a neutral pH, the amino terminus of the peptide can be preferentially labeled. Briefly, the peptide (at a concentration of 1-3 mg/ml) will be incubated with a Xenobind plates for 2 hours in 50 mM sodium phosphate buffer, (pH 7.0). Following rinsing with wash buffer, the plates will be blocked with 3% bovine serum albumin for 2 hours at 37° C. Finally the plates will be rinsed three times in wash buffer and stored at 4° C. until use.

Optionally unoccupied reactive sites on the microtiter plate or on the food packaging are blocked by coupling bovine serum albumin, or the active domain of p26 thereto. p26 is an alpha-crystallin type protein that is used in this case to reduce non specific protein aggregation. The ability of the p26 protein to refold heat denatured citrate synthetase before and after coupling to the surface of the food packaging is used as a control for determining p26 activity. Alpha-crystallin type proteins were recombinantly produced using standard recombinant DNA technologies (Maniatis et al., Molecular cloning: a laboratory manual. 1982). Briefly, the plasmid containing the beta sheet-charged core domain of p26 is electroporated into electrocompetent B121 (DE3) cells ([Bio-Rad] BIO-RAD *E. coli* pulser). The cells are grown up to an OD of 0.8, then induced with 1 mM IPTG for 4 hours. The cells are spun down, and sonicated in low buffer (10 mM Tris, pH 0.8, 500 mM NaCl, 50 mM Imidizole) to lyse (Virsonic, Virtis, Gardiner, N.Y.). The lysate is spun down at 13,000×g for 10 minutes, and the supernatant 0.45 and 0.2 μm filtered. This filtrate is loaded onto a Ni-NTA superose column ([Qiagen] QIAGEN, Valencia, Calif., cat # 30410). High buffer (10 mM Tris pH 8.0, 500 mM NaCl, 250 mM Imidizole) is used to elute the protein.

EXAMPLE I

Rapid *Listeria monocytogenes* Detection at the Wholesale Level

Food products were tested in pentuplicate to determine the range of applicability for ready to eat food products. Each solid food sample was processed in a laminar flow hood. Twenty-five grams of each food product were removed from its package and weighed. The weighed sample of the solid food was placed in a sterile stomacher bag with 125 ml of phosphate-buffered saline (PBS, 10 mM potassium phosphate, pH 7.4, 120 mM sodium chloride, 2.7 mM potassium chloride). Solid food was homogenized in a stomacher blender (Fisher Scientific; Pittsburgh, Pa.) and the filtered supernatants were used for testing. *L. monocytogenes* was captured and efficiently released by adding a plurality of Protein Encapsulated Styrofoam Tablets. PES tablets (described above) were incubated with the food extract for at least a 30 minute incubation period. The PES tablet were removed from the surface and placed in enrichment media to efficiently release the bacteria. After incubating at 37° C. for at least 4 hours, the media was spun down at 5,000×g for 10 minutes, and the pellet was resuspended in 50 μl of PBS. Liquid foods were prepared by mixing an aliquot of the liquid food with one of the PES tablets without stomaching the liquid. After the 30 minute capture step, the PES tablet was recovered and the pellet was placed in enrichment media.

A protease based assay was performed on each sample. Each well in the microtiter plate was read before starting the assay in order to get an accurate measurement of the background to control for well to well variability. The protease assay was performed using microtiter plates having FRET labeled peptide such as M1 that is described above. Typically 0.5 pg of peptide was incubated with 50 μl of bacterial culture extract for at least 20 min at 37° C. In the presence of bacteria the FRET peptide will fluoresce at 493 nm. As positive controls, either *L. monocytogenes* or the active recombinant form of the pathogen specific protease can be added to some of the food samples prior to incubation in the microtiter plate assay. Negative controls consist of food samples that are determined to be devoid of bacterial pathogens based on existing published methods (Curtis et al., 1995).

EXAMPLE 2

Rapid *Listeria monocytogenes* Detection of Bacteria for Home Use

PVDF is a blotting membrane that is hydrophobic until soaked in methanol, when it becomes hydrophilic. A ring of methanol was stamped on PVDF and allowed to air dry. A peptide substrate labeled with an FD&C approved dye was incubated with the membrane. It only bound to the hydrophilic ring. This membrane was attached to packaging material, for example the inside of food packages in direct contact with the food. If the peptide is cleaved by bacterial proteases in the food, the dye molecule will be attracted to the hydrophobic region of the membrane, and concentrate there, indicating that bacteria is present by the formation of color or florescence within the center of the ring. Bacteria other than *Listeria monocytogenes* can be detected using the described method and device once a specific protease substrate interaction has been determined and optimized for the bacterium of interest.

For some bacterial species, it may be necessary to provide a method of optimizing substrate-protease interaction. For example, divalent cations may be required to optimize protease cleavage of the coupled substrate. In this case, the food packaging surface will be blocked with proteins and/or peptides that can be precharged with metal ions, such as for example polyhistidine or zinc finger motifs.

One of ordinary skill in the art will appreciate further features and advantage of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of detecting *Listeria monocytogenes* in a test sample, said method comprising the steps of:

a) contacting the test sample with a peptide substrate for a protease that is unique to *Listeria monocytogenes*, wherein said peptide substrate comprises the sequence of SEQ ID NO:1, further comprising a fluorescent or chromagenic label and;

b) determining cleavage of the labeled peptide substrate or absence of cleavage of the labeled peptide substrate based on detection of said label, wherein the detection of said label is indicative of peptide substrate cleavage, and wherein peptide substrate cleavage is indicative of the presence of *Listeria monocytogenes* in the test sample, and absence of cleavage of the peptide substrate is indicative of the absence of *Listeria monocytogenes* in the test sample.

2. The method of claim 1, wherein the fluorescent label comprises a fluorophore and a quencher.

3. The method of claim 2, wherein the fluorescent label is detected using a fluorimeter or a UV lamp.

4. The method of claim 1, wherein if the chromagenically labeled peptide substrate is cleaved, a colorimetric signal is detected by a colorimeter.

5. The method of claim 1, wherein the labeled peptide substrate is attached to a solid surface.

6. The method of claim 5, wherein the solid surface is glass or polypropylene.

* * * * *